(12) United States Patent
Singer et al.

(10) Patent No.: US 11,371,827 B2
(45) Date of Patent: Jun. 28, 2022

(54) MULTIPLE SCALE ANALYSIS OF CORE SAMPLE TO ESTIMATE SURFACE ROUGHNESS

(71) Applicant: Halliburton Energy Services, Inc., Houston, TX (US)

(72) Inventors: Gabriela Singer, Richmond, TX (US); Lilong Li, Houston, TX (US); Songhua Chen, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 271 days.

(21) Appl. No.: 16/753,928

(22) PCT Filed: Jun. 11, 2019

(86) PCT No.: PCT/US2019/036592
§ 371 (c)(1),
(2) Date: Apr. 6, 2020

(87) PCT Pub. No.: WO2020/251555
PCT Pub. Date: Dec. 17, 2020

(65) Prior Publication Data
US 2021/0404789 A1    Dec. 30, 2021

(51) Int. Cl.
*G01R 33/60* (2006.01)
*G01B 7/34* (2006.01)
(Continued)

(52) U.S. Cl.
CPC ............. *G01B 7/34* (2013.01); *G01N 5/02* (2013.01); *G01N 24/081* (2013.01); *G01N 33/24* (2013.01); *G01R 33/448* (2013.01)

(58) Field of Classification Search
CPC .............. G01R 33/543; G01R 33/5608; G01R 33/4828; G01R 33/3415; G01R 33/283;
(Continued)

(56) References Cited

U.S. PATENT DOCUMENTS

| 2013/0182819 A1 | 7/2013 | Dvorkin et al. |
| 2015/0323516 A1* | 11/2015 | Washburn ............ G01N 33/241 436/32 |

(Continued)

FOREIGN PATENT DOCUMENTS

| WO | 2012084220 A1 | 6/2012 |
| WO | 2013151985 A2 | 10/2013 |

OTHER PUBLICATIONS

PCT Application Serial No. PCT/US2019/036592, International Search Report, dated Mar. 5, 2020, 3 pages.
(Continued)

*Primary Examiner* — Jermele M Hollington
*Assistant Examiner* — Taqi R Nasir
(74) *Attorney, Agent, or Firm* — Delizio, Peacock, Lewin & Guerra (57) ABSTRACT

Measurements of a core sample at scales of measurement that differ by multiple orders of magnitude can be used to calculate a value that fairly represents surface roughness of the core sample. This surface roughness value can be used to determine petrophysical properties of the subsurface formation from which the core sample was obtained. The measurements can be nuclear magnetic resonance (NMR) diffusion-relaxation and gas-adsorption measurements. Surface relaxivities at the different scales are determined from the measurements and a ratio those surface relaxivities can be used to calculate the surface roughness value.

20 Claims, 8 Drawing Sheets

(51) Int. Cl.
  *G01N 5/02* (2006.01)
  *G01N 24/08* (2006.01)
  *G01N 33/24* (2006.01)
  *G01R 33/44* (2006.01)

(58) Field of Classification Search
  CPC .... G01R 33/307; G01R 33/60; G01R 33/448; G01V 3/32; E21B 49/08; E21B 2049/085; G01N 24/10; G01N 5/02; G01N 24/081; G01N 33/24; G01B 7/34
  See application file for complete search history.

(56) References Cited

U.S. PATENT DOCUMENTS

2015/0323517 A1* 11/2015 Washburn ............ G01N 33/246 73/73
2017/0082549 A1* 3/2017 Washburn ............ G01N 15/088
2018/0328905 A1* 11/2018 Jacobi ................. G01N 33/241

OTHER PUBLICATIONS

PCT Application Serial No. PCT/US2019/036592, International Written Opinion, dated Mar. 5, 2020, 7 pages.
Hurlimann, et al., "Restricted Diffusion in Sedimentary Rocks, Determination of Surface-Area-to-Volume Ratio and Surface Relaxivity", Journal Of Magnetic Resonance, Series A 111, Jan. 1994, pp. 169-178.
Nordin, et al., "The Effect of Surface Roughness on Nuclear Magnetic Resonance Relaxation", The Open-Access Journal for the Basic Principles of Diffusion Theory, Experiment Application, 2016, 11 pages.
Zielinski, et al., "Restricted Diffusion Effects in Saturation Estimates From 2D Diffusion-Relaxation NMR Maps", Society of Petroleum Engineers, 2010, 8 pages.

* cited by examiner

MULTIPLE SCALE ANALYSIS OF CORE SAMPLE TO ESTIMATE SURFACE ROUGHNESS

TECHNICAL FIELD

The disclosure generally relates to the field of obtaining materials from wells, particularly to, investigating or analyzing materials by determining their chemical or physical properties (measuring or testing processes other than immunoassay, involving enzymes or microorganisms).

BACKGROUND

Core analysis of subsurface samples provides a means of measuring reservoir rock samples, also known as core samples, to determine formation properties such as surface roughness, permeability, porosity, and other characteristics of the formation/borehole. Such core analysis is useful for well log calibration and for providing direct evidence of the presence, distribution, and deliverability of hydrocarbons. One such method of determining surface roughness is through atomic force microscopy (AFM). In AFM a cantilever having a sharp tip at the end moves the tip along the surface of the core sample. A beam of laser is reflected off the cantilever into a photo-detector while the tip travels along the surface. AFM measures the vertical and lateral deflections that results from surface roughness by measuring the positional change of the laser beam in the photo-detector. Another method of obtaining surface roughness of a core sample is using a scanning electron microscope (SEM). In SEM a beam of high-energy electrons is directed at the surface of the sample. When the accelerated electrons hit the surface of the sample, the energy it carries is dissipated and generates a variety of signals through the electron-sample interaction. One type of such interaction is the generation of secondary electrons, which are electrons emitted by atoms near the surface of a sample material after it has been excited and have gained sufficient energy to escape the sample surface. These signals can be used to generate an image of the surface topology which in turn can be used to calculate surface roughness.

BRIEF DESCRIPTION OF THE DRAWINGS

Embodiments of the disclosure may be better understood by referencing the accompanying drawings.

DESCRIPTION OF EMBODIMENTS

The description that follows includes example systems, methods, techniques, and program flows that embody embodiments of the disclosure. However, it is understood that this disclosure may be practiced without these specific details. For instance, this disclosure refers to nuclear magnetic resonance (NMR) diffusion-$T_2$ (D-$T_2$) or diffusion-$T_1$ (D-$T_1$) technique and Brunauer-Emmett-Teller (BET) technique in illustrative examples. Embodiments of this disclosure can be also applied to other NMR and gas-adsorption methods. In other instances, well-known instruction instances, protocols, structures and techniques have not been shown in detail in order not to obfuscate the description.

Overview

Surface roughness can be measured with devices and techniques that scan the outer surface of a core sample. Examples of these devices and techniques include atomic force microscopy (AFM), stylus profilometers, scanning electron microscope (SEM), and other optical methods directed towards the outer surface of the sample. In such methods, only the surface roughness measured from the outer surface of the sample is used and therefore may be a poor representation of the entire core sample, which represents the formation from which it was obtained. Furthermore, some methods, such as AFM and stylus methods that utilize a needle in contact with the surface, may damage the core sample. Optical methods that are non-invasive, such as measuring the bi-directional reflection distribution function (BRDF), may be limited by the optical properties of the core sample. A non-invasive bulk measurement method that determines the surface roughness representative of the entire core sample provides a more accurate representation of a sample's surface roughness and other derivative properties without damaging the core sample.

Multiple scale analysis of a core sample obtains values at different average length-scales that can be used to calculate a value that represents surface roughness or an estimate of surface roughness of a formation from which the core sample was obtained. Since multiple analysis techniques would be applied to the core sample, at least the initial analysis cannot destroy the core sample. The different average length-scales of the multiple analysis techniques can be multiple orders of magnitude apart. For example, a first scale of analysis can be that of nuclear magnetic resonance (NMR) diffusion with measurements in micrometers and a second scale of analysis can be that of gas-adsorption at a molecular level measured in nanometers. Combining measurements from an NMR diffusion-relaxation technique (e.g., such as diffusion-$T_2$ or diffusion-$T_1$) with measurements from a gas-adsorption technique (e.g., the Brunauer-Emmett-Teller (BET)) allows for a more representative determination of surface roughness for a formation based on bulk measurements of a subsurface sample. There is an inherent difference in the average length-scale between BET and NMR diffusion-relaxation techniques that leads to two different surface relativities measured by performing the two techniques, $\rho_{DT2}$ and $\rho_{BET}$. By exploiting this inherent difference in the average length-scale measurements techniques and the corresponding surface relativity values, the surface roughness can be determined.

Surface roughness may also be linked to wettability which in turn affects relative permeability, electrical properties, nuclear magnetic resonance relaxation times and saturation profiles in the subsurface formation. Such core analysis provides important information useful in determining the optimal values for various parameters during formation drilling and hydrocarbon production such as when to drill, what a target depth for fracturing should be, which wells to inject with fluids, etc.

Example Well System

Figure 1:
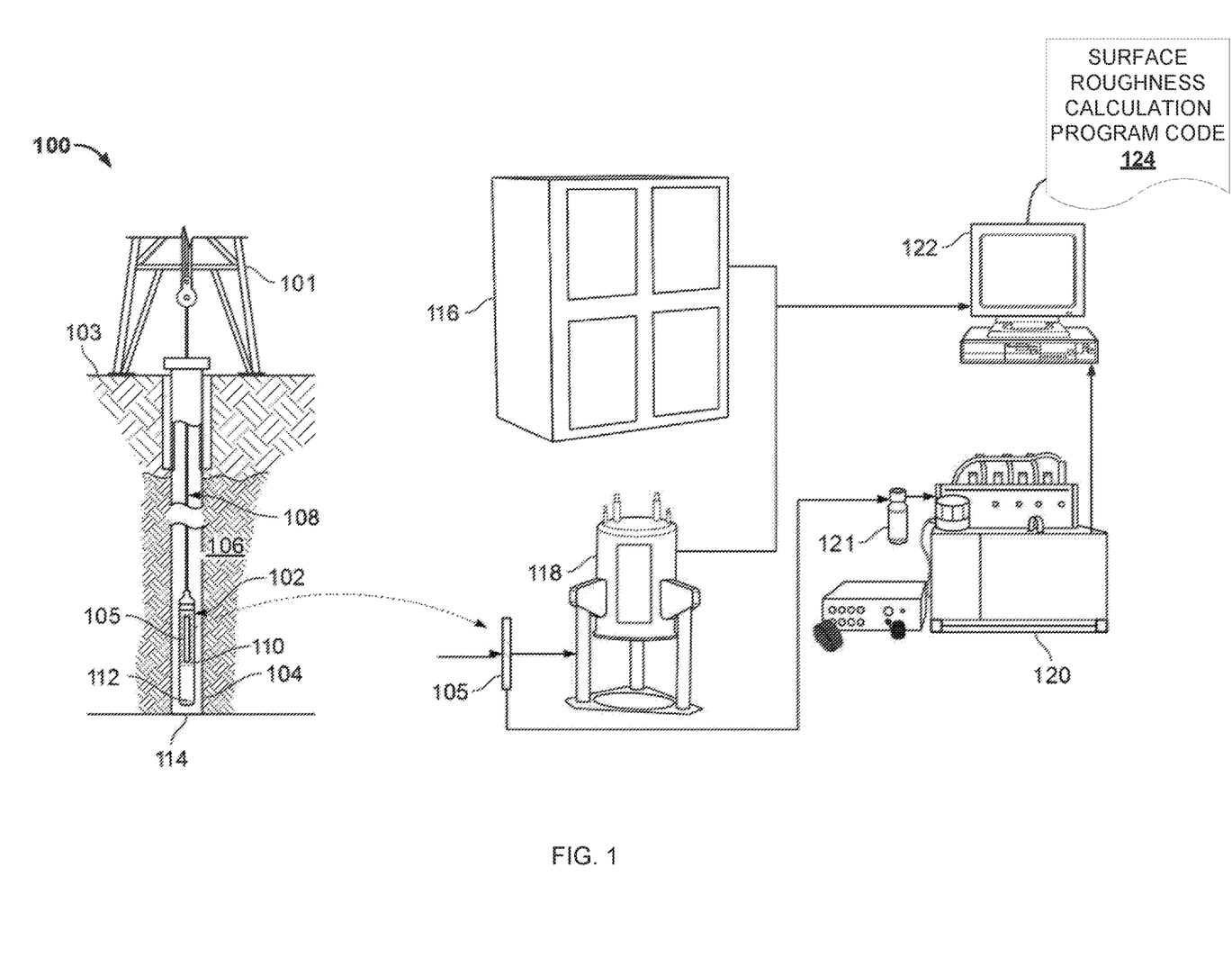
FIG. 1 depicts an example coring and sample analysis system for collecting a core sample for a hybrid surface roughness determination technique.

FIG. 1 shows an example coring and sample analysis system for collecting core sample for a hybrid surface roughness determination technique that combines measurements from an NMR diffusion-relaxation technique and a gas-adsorption technique. In FIG. 1, a coring and sample analysis system 100 comprises a coring tool 102. The coring tool 102 is placed in a wellbore 104 by a rig 101 penetrating a subterranean formation 106 by a conveyance, illustrated as a wireline 108 conveyance. The coring tool 102 includes a core holder 110 and corehead 112. The corehead 112 drills through the bottom of the wellbore 114 to deposit a core sample 105 of the subterranean formation 106 into the core holder 110, which is then transported to the surface 103 for analysis. In certain example embodiments, the coring tool 102 is placed in the wellbore 104 by a different conveyance (e.g., coil tubing, wired coiled tubing, slickline, and the like) that is connected to the surface 103.

After obtaining a core sample 105, the core sample is prepared for analysis and then analyzed with a combination of NMR diffusion-relaxation and gas-adsorption to capture characteristics of the core sample on different scales of measurement to facilitate calculating a more representative surface roughness measurement for the formation 106 with the core sample 105. The analysis components of the coring and sample analysis system 100 comprises NMR equipment that contains at least in part a spectrometer 116 and a magnetizing assembly 118 that includes a magnet(s) equipped with pulse field gradient(s) or fixed field gradient and a case or holder for a core sample. The NMR equipment is used to analyze a core sample and obtain NMR diffusion-relaxation measurements/values. Additionally, the system 100 is comprised of a volumetric gas-adsorption apparatus 120 capable of performing a gas-adsorption analysis on a subsample 121 of the sample 105. A small subsample 121 (e.g., 5 grams) is collected from the core sample 105 and crushed. Mass of the subsample 121 is then measured and degassed using vacuum and heat. A computer 122 processes the information obtained from the NMR equipment and information obtained from the volumetric gas-adsorption apparatus 120. The computer 122 is programmed to perform calculations with results from NMR diffusion-relaxation analysis and gas-adsorption analysis to obtain a value(s) that represents surface roughness across different scales of measurement corresponding to the different sample analysis techniques.

Modifications, additions, or omissions can be made to the example system described in FIG. 1 without departing from the scope of the present disclosure. For example, the coring tool 102 can include a sidewall coring tool where the core samples 105 would be removed from the side of the wellbore 104 from a hole that has already been drilled. Sidewall coring may involve firing a hollow bullet into the sidewall rock formation of the drilled hole to create a core sample. Moreover, components can be added to or removed from the drilling system 101 without departing from the scope of the present disclosure. For example, a ball check valve, swivel assembly, stabilizer, shoe assembly, and various coreheads types such as thermally stable polycrystalline (TSP) corehead, full diamond impregnation coreheads, polycrystalline diamond compact (PDC) coreheads may be added.

In another embodiments, the coring and sample analysis system 100 may not use any coring device to obtain the core sample, but rather would substitute drilling cuttings as core samples. Drilling cuttings may be obtained through a drilling string comprised of drill pipe, bottom-hole assembly, bit, and others. The subterranean layer of a certain position associated with the drilling cuttings can be determined through measuring the duration, logging-while-drilling (LWD) well logs, and other information obtained through a wireline tool.

Example Operations

Figure 2:
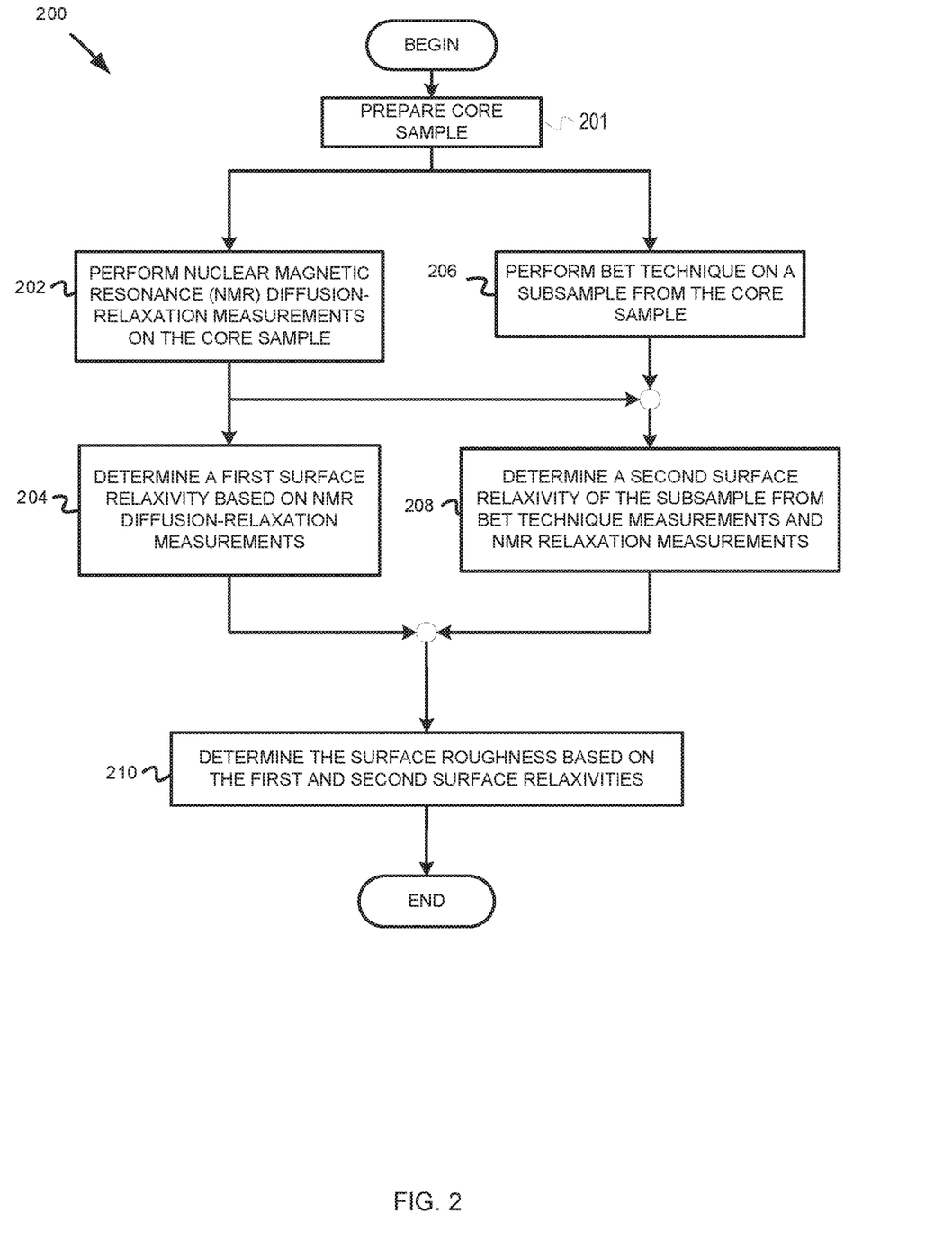
FIG. 2 depicts a flowchart of operations for a hybrid surface roughness determination technique that combines measurements from an NMR diffusion-relaxation-technique with a gas-adsorption technique.

FIG. 2 depicts a flowchart of operations for a hybrid surface roughness determination technique that combines measurements from an NMR diffusion-relaxation technique and a gas-adsorption technique. Flowchart 200 of FIG. 2 include operations that can be performed by hardware, software, firmware, or a combination thereof. For example, at least some of the operations can be performed by a processor executing program code or instructions. In some embodiments, such operations can be performed in a computer at the surface.

At block 201, a core sample is prepared for NMR diffusion-relaxation analysis and gas-adsorption analysis. Preparation of the core sample can be done differently and some aspects depend upon state of the core sample as described below. For instance, preparing the core sample for the two different analysis can be: 1) drying the core sample; 2) cut an end of the dried core sample as a subsample for the gas-adsorption analysis; and 3) then separately prepare the core sample for the NMR diffusion-relaxation analysis and the subsample for the gas-adsorption analysis. As another example of preparing the core sample, preparing may be: 1) prepare the core sample for NMR diffusion-relaxation analysis depending upon state of the core sample (i.e., water wet, oil wet, mix-wet), 2) dry the core sample after the NMR diffusion-relaxation analysis; and 3) collect the subsample from the dried core sample after the NMR diffusion-relaxation analysis.

At block 202, the hybrid technique performs nuclear magnetic resonance (NMR) diffusion-relaxation measurements on the core sample. The NMR diffusion-relaxation measurements involve saturating the sample with a fluid to achieve one hundred percent saturation. For instance, the core sample is 100% saturated with a 100% wetting fluid. For water-wet core samples, a brine solution is used to fully saturate the sample. For oil-wet core samples, a refined oil, such as dodecane, is used to fully saturate the core sample. For a mixed-wet core, the core sample is cleaned before being dried, and then saturated with brine. An external magnetic field is then applied to the prepared sample and a 2D NMR diffusion-relaxation measurement is performed (pulsed field gradient or fixed field gradient version followed by a Carr-Purcell-Meiboom-Gill (CPMG) pulse sequence) to determine the 2D diffusion-relaxation map (D-$T_2$ or D-$T_1$). A 1D relaxation distribution can be obtained from the 2D diffusion-relaxation NMR data projection on the $T_2$ (or $T_1$) axis. This 1D distribution is missing the signal below about 10 ms (the experimental diffusion time, $\Delta$). Instead, a 1D NMR relaxation measurement can be acquired on the sample before or after the 2D diffusion-relaxation measurement. If the 1D relaxation extracted from the D-$T_2$ is used for the BET analysis and if the sample has a fast decaying signal, that signal will be missed and therefore, the log-mean and mean relaxation times will be overestimated and the surface relaxivity $\rho_{BET}$ will be underestimated.

At block 204, the hybrid technique determines the surface relaxivity of the sample from the NMR diffusion-relaxation measurements. Surface relaxivity can be found by using the Padé (or other) approximation, Equation (1), which describes the relationship between time-dependent diffusion coefficients for short and long time periods. $D(T_2)$ is the time-dependent diffusion coefficient of fluid molecules diffusing in the pore space of the core sample. In determining the diffusion coefficient, $T_1$ may also be used instead of $T_2$ so far as the corresponding measurements and variables also use $T_1$.

$$D(T_2) = D_0 \left[ 1 - \gamma \frac{\alpha L_D + \gamma \left(\frac{L_D}{L_M}\right)^2}{\alpha L_D + \gamma \left(\frac{L_D}{L_M}\right)^2 + \gamma} \right] \quad (1)$$

The variables in Equation (1) are defined by Equations (2)-(4) below.

$$\alpha = \frac{4}{9\sqrt{\pi}} \frac{1}{T_{2S} \rho_{DT2}} \quad (2)$$

$$L_D = \sqrt{D_0 \Delta} \quad (3)$$

$$\gamma = 1 - \frac{D_\infty}{D_0} = 1 - \varphi^{m-1} \quad (4)$$

$\alpha$ is defined by the Equation (2) and consists of time constant, $T_{2S}$ (or $T_{1S}$), which describes the contribution of surface relaxivity to the relaxation time of fluid in a rock. The surface relaxivity value, $\rho_{DT2}$, describes the surface relaxivity obtained through NMR diffusion-relaxation measurement. The length-scale of diffusion, $L_D$, is defined by Equation (3) where $D_0$ is the bulk diffusion coefficient of the fluid used to saturate the sample at block 202 and $\Delta$ is the diffusion time. $\gamma$ is defined in Equation (4) where $D_\infty$ is the diffusion coefficient in the tortuosity limit, $\varphi$ is the porosity, and m is the cementation coefficient determined from electrical measurements (the Padé fit is sensitive to m value).

In a typical core sample, the length-scale of the heterogeneity of the system, $L_M$, is significantly greater than the length-scale of diffusion and therefore Equation (1) can be reduced to the following.

$$D(T_2) = D_0 \left[ 1 - \gamma \frac{\alpha L_D}{\alpha L_D + \gamma} \right] \quad (5)$$

Figure 3:
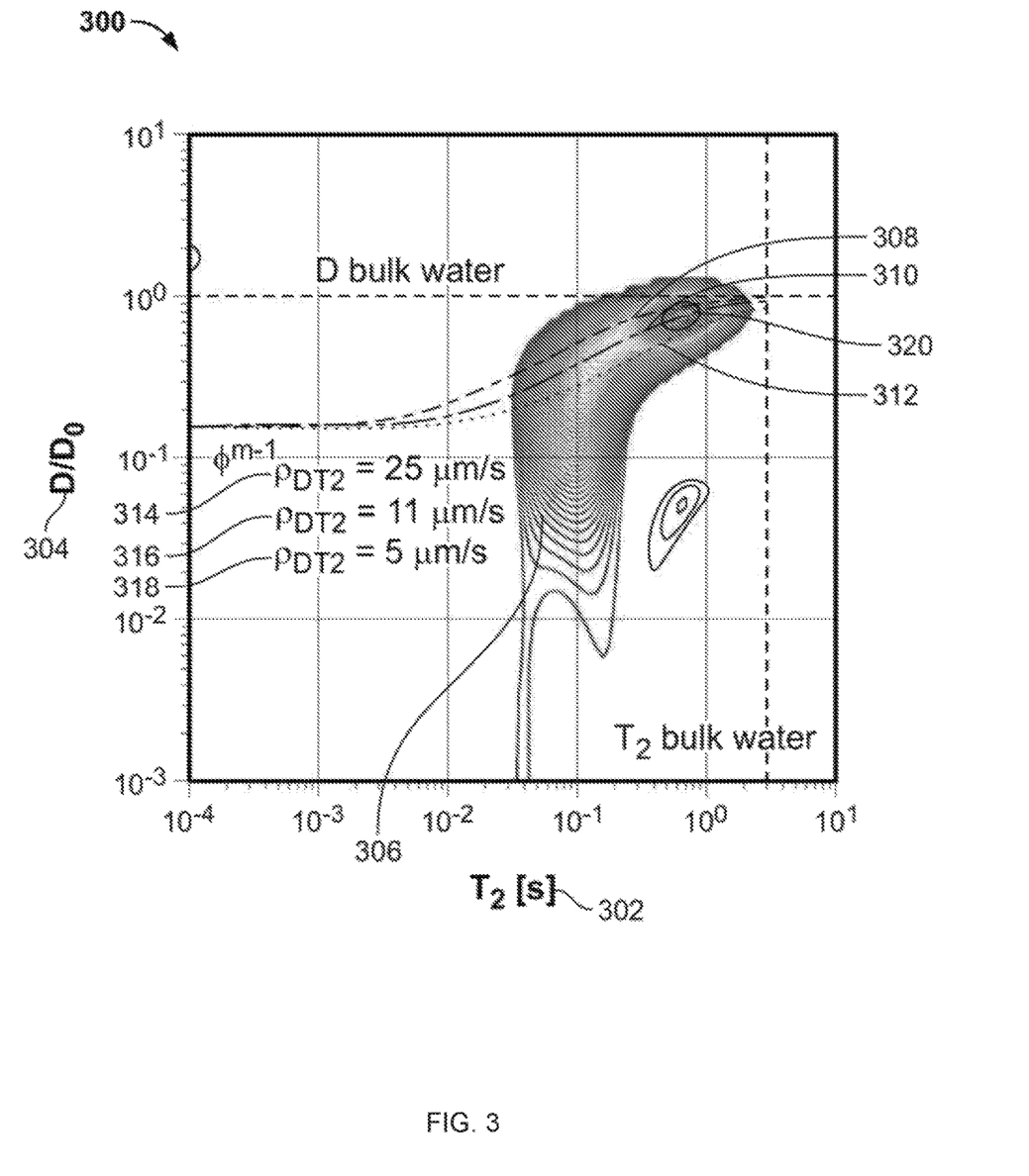
FIG. 3 depicts a graph of a sample NMR D-$T_2$ measurements used to determine surface relaxivity from a best fit.

Data obtained at block 202 is used to generate an NMR graph where upon Equation (5) may be plotted to determine the surface relaxivity from the D-$T_2$ (or D-$T_1$) NMR. To illustrate, FIG. 3 depicts a graph 300 of a sample NMR D-$T_2$ measurements used to determine surface relaxivity of best fit. The graph 300 is composed of relative diffusion coefficient 302 on the y-axis and transverse relaxation time 304 on the x-axis. The contour lines of various shades 306 represent the NMR signals of constant amplitude. To determine the surface relaxivity, three dotted lines 308, 310, 312 of differing shades having respective surface relaxivity values 314, 316, 318 are plotted in the graph 300 to determine what surface relaxivity value would have the best fit. Dotted line 310 with the surface relaxivity value 316 of 11 μm/s cross the region of highest signal strength 320 and therefore gives the surface relaxivity from NMR diffusion technique. Modifications, additions, or omissions to the example graph 300 described in FIG. 3 that uses longitudinal relaxation time ($T_1$) measurements instead of transverse relaxation time ($T_2$) to identify the surface relaxivity do not depart from the scope of the present disclosure.

At block 206, the hybrid technique performs the BET technique on the core sample. This can be done concurrently with obtaining the NMR diffusion relaxation measurements as illustrated in FIG. 2. This BET technique involves preparing a subsample of the dried core sample, by crushing the subsample, measuring its mass, and degassing the subsample using vacuum and heat. For example, a 5 gram subsample is taken from a 50 gram core sample before fluid saturation of the core sample. The BET analysis instrument then measures the volume of gas, typically nitrogen, adsorbed to the surface of the crushed subsample. The BET analysis instrument introduces known quantities of ultra-pure nitrogen gas into the subsample while recording the relative pressure, $P/P_0$, and the weight of the gas adsorbed.

At block 208, the hybrid technique determines the surface relaxivity of the sample from BET technique measurements. The BET relation is given by Equation 6, where W is the weight of the gas adsorbed, $W_m$ is the weight of adsorbate as monolayer, and C is the BET constant.

$$\frac{1}{W\left(\frac{P_0}{P} - 1\right)} = \frac{1}{W_m C} + \frac{C-1}{W_m C}\left(\frac{P}{P_0}\right) \quad (6)$$

The surface area per unit weight of the core sample, $S_g$, is described by Equation (7) where $N_A$ is the Avogadro's number, M is the molecular weight of the adsorbate, and $A_{cs}$ is the adsorbate cross sectional Area, and $M_g$ is the sample weight.

$$S_g = \frac{W_m N_A A_{CS}}{M_g M} \quad (7)$$

The surface to pore-volume ratio, $S/V_p$, is then given by Equation (8) where $\rho_g$ is the grain density and $\varphi$ is the porosity.

$$\frac{S}{V_p} = \frac{1-\gamma}{\gamma}\frac{S}{V_g} = \frac{1-\varphi}{\varphi}\rho_g S_g \quad (8)$$

The relaxation rate of fluids in porous media is dominated by the fluid-solid interaction in the pore space and the relaxation rate the relaxation rate $1/T_2$ is proportional to the surface to pore-volume ratio. Therefore, this relationship is given below in Equation (9)

$$\frac{1}{T_2} = \rho \frac{S}{V_p} \quad (9)$$

Equation (10) combines Equations (7)-(9) to describe the equation for the surface relaxivity from BET gas-adsorption technique. Moreover, in the described equations $T_2$ may be substituted by $T_1$ so far as the relaxation time matches the type used in the NMR diffusion-relaxation technique in blocks 202 and 204.

$$\rho_{BET} = \frac{1}{T_2}\left(\frac{\gamma}{1-\gamma}\right)\frac{1}{\rho_g S_g} \qquad (10)$$

Figure 4:
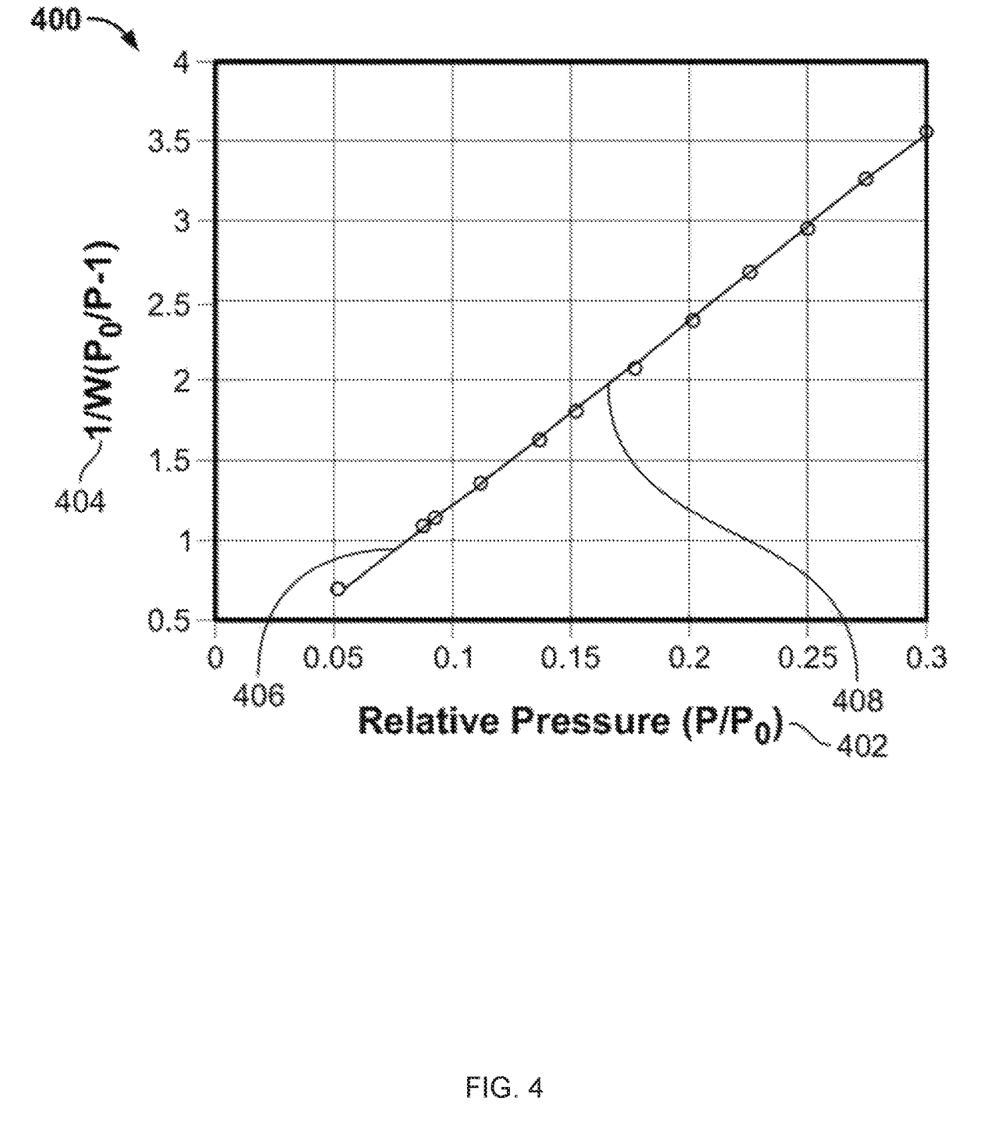
FIG. 4 depicts a graph of a sample BET surface area plot measured by the BET analysis instrument.

Data obtained at block 206 is used to generate a multi-point BET surface area plot to determine the weight of adsorbate as monolayer described by Equation (6). To illustrate, FIG. 4 depicts a graph 400 of a BET surface area plot measured by the BET analysis instrument. The graph 400 is composed of the relative pressure 402 on the x-axis and the BET value, $1/W(P_0/P-1)$, on the y-axis. The graph 400 contains data points 406 obtained through the BET analysis instrument and the recorded relative pressure and the weight of the gas adsorbed. A linear plot 408 can be generated through multiple data points 406 to solve Equation (10). By using linear regression analysis, the slope and the intercept are determined and the weight of adsorbate as monolayer can be found.

Figure 5:
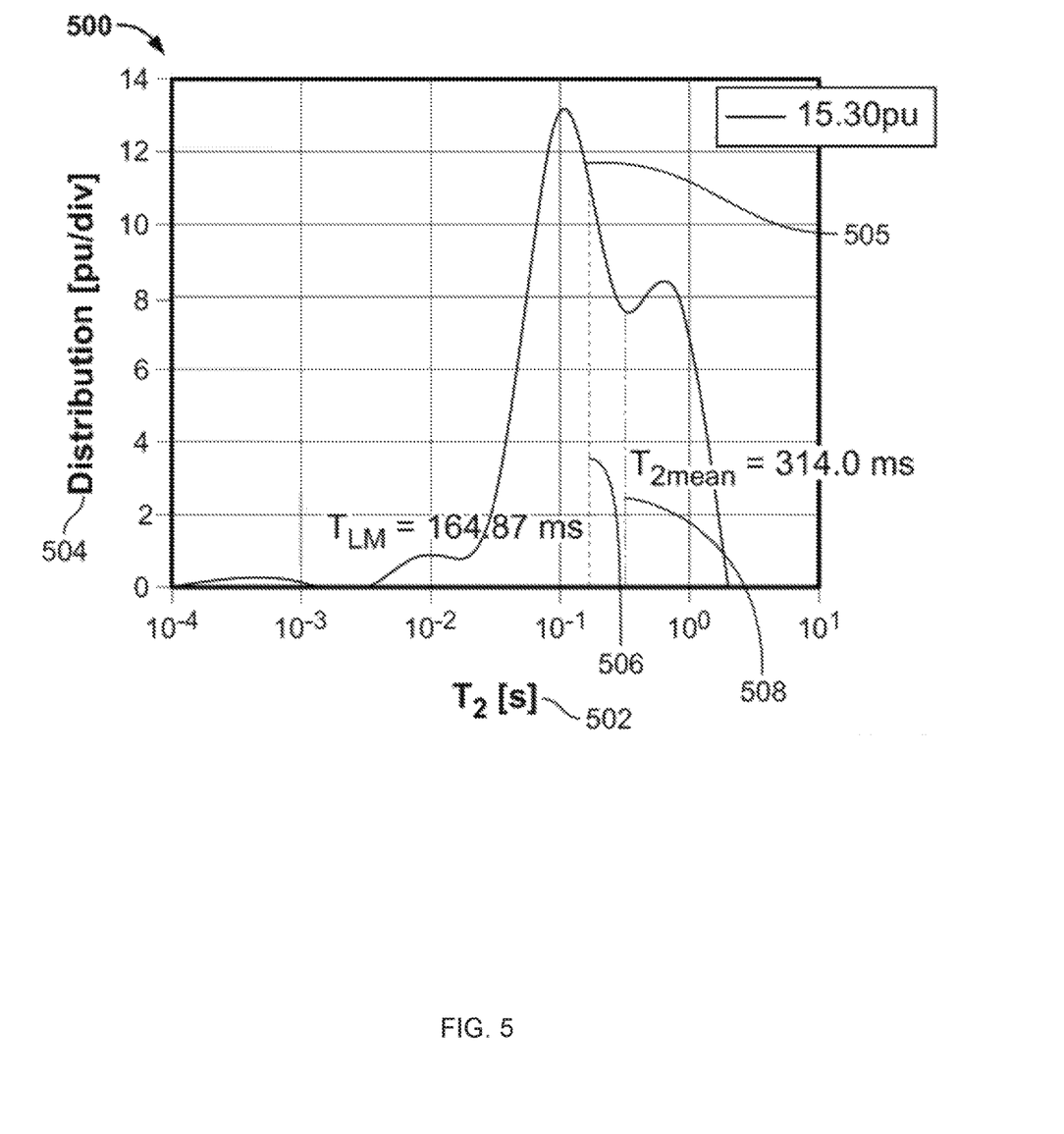
FIG. 5 depicts a graph of a sample $T_2$ distribution plot.

Data obtained at block 202 is also used to generate a $T_2$-distribution plot or $T_1$-distribution plot to determine the relaxation time value required to solve for Equation (10). To illustrate, FIG. 5 depicts a graph 500 of a $T_2$ distribution plot composed of transverse relaxation time 502 on the x-axis and NMR distribution 504 on the y-axis obtained. Through measuring the surface area underneath the line 505 generated from data obtained at block 204, both log-mean value 506 of the $T_2$ distribution or the mean value 508 of the $T_2$ distribution can be obtained. Modifications, additions, or omissions to the example graph 500 described in FIG. 5 that uses longitudinal relaxation time ($T_1$) measurements instead of transverse relaxation time ($T_2$) to identify the relaxation time necessary for Equation (10) do not depart from the scope of the present disclosure. Using the weight of adsorbate as monolayer and relaxation time value (either mean or log-mean value consistent with the scale used in D-$T_2$ or D-$T_1$ measurements at block 204) the surface relaxivity of the sample from BET technique measurements can be calculated.

At block 210, the hybrid technique determines surface roughness based on the two surface relaxivities obtained from NMR diffusion-relaxation and BET technique measurements at blocks 204 and 208. The measured area of a rough surface depends on the averaging length-scale of the technique used for the measurement. In NMR diffusion-relaxation measurements such as D-$T_2$ or D-$T_1$ correlation maps, the averaging length-scale equals the diffusion length $L_D$. Typically, $L_D=10$ μm, which is a function of the diffusion coefficient of the bulk fluid ($D_0$) and the diffusion evolution time (Δ). For gas-adsorption measurements like the BET technique, the averaging length-scale equals the size of the molecular $d_{N2}$, where $d_{N2}=0.155$ nm for Nitrogen ($N_2$). This difference in averaging length-scale between BET and DT2 measurements can be exploited to determine the surface roughness. In NMR diffusion-relaxation the surface relaxivity is not sensitive to the surface roughness below the averaging length-scale of 10 μm. The surface relaxivity from BET on the other hand is not sensitive to the surface roughness below the averaging length-scale of 0.155 nm. The ratio of the two surface relaxivity values can be used as a measure of the effect of surface roughness of the bulk sample.

For most core samples with rough surfaces, the pore size derived from the surface relaxation can differ by orders of magnitudes from the actual pore size. Moreover, when surface roughness is present, the surface relaxivity is independent of the shape of the surface pores and strongly dependent on the ratio of depth to width of the surface pores. The roughness of the core sample surface is considered to be generated by accounting for surface modulations by approximating them through any geometric shape, for example a cylinder. Because the effective relaxivity is largely insensitive to the shape of the roughness, cylinders can be used to describe the shape of each surface roughness. Thus, in the fast diffusion regime, the following Equation 11 describes the relationship between the two relaxivities by factoring in the effect of surface roughness, where L is the height of the cylinder and d is the diameter of the cylinder. The variable f is the percentage of flat surface that is covered by cylinders.

$$\rho_{DT2} = \rho_{BET}\left(1 + \frac{2fL}{d}\right) \qquad (11)$$

Equation (11) can now be rearranged into Equation (12) to solve for surface roughness, L/d, described below.

$$\frac{L}{d} = \frac{\left(\frac{\rho_{DT2}}{\rho_{BET}} - 1\right)}{2f} \qquad (12)$$

The surface roughness therefore is calculated by accounting for the impact of surface modulations on the surface roughness as a ratio of $\rho_{DT2}$ and $\rho_{BET}$.

Modifications, additions, or omissions can be made to the example hybrid technique described in FIG. 2 without departing from the scope of the present disclosure. For example, the order in which the two analysis techniques, gas-adsorption and NMR diffusion-relaxation, are performed may be switched or occur in parallel. Thus, block 206 may be performed before blocks 202 and 204 or be performed concurrently. To perform the two methods in parallel, a small portion of the core sample, typically about 5 grams, may be removed from the core sample before the fluid saturation described in block 202.

Figure 6:
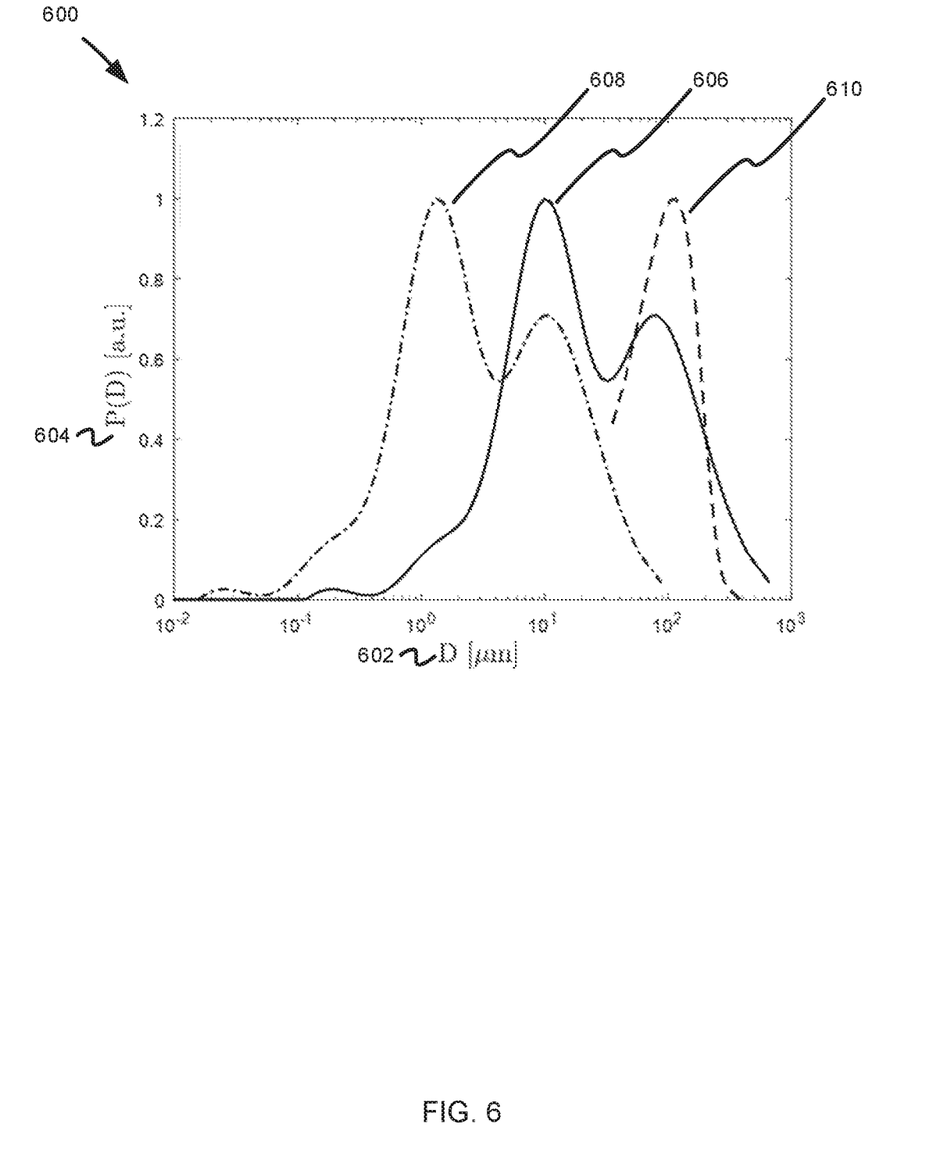
FIG. 6 depicts a sample pore size distribution plot depicting correlation between $\rho_{BET}$, $\rho_{DT2}$, and computed tomography (CT) scanning.

To illustrate, FIG. 6 depicts a sample pore size distribution plot 600 depicting correlation between $\rho_{DT2}$ and computed tomography (CT) scanning. In plot 600, the computed surface roughness (L/d) from $\rho_{BET}$ and $\rho_{DT2}$ (Equation 12, assuming f=1) is determined to be 3.24 for this example. This value concurs with surface roughness measured by microscopy technique, such as Laser Confocal Scanning Microscopy, which is determined to be 3.2 in this example. The distribution plot 600 is composed of diameter of pores 602 on the x-axis and the pore size distribution 604 on the y-axis. Pore size distribution estimated using $\rho_{DT2}$ 606 shows that the large pore size shows high degree of correlation with pore size estimated from CT scanning as depicted by pore size distribution estimated using CT scanning 610 whereas the pore size distribution estimated using $\rho_{BET}$ 608 shows that using $\rho_{BET}$ underestimates the pore diameters.

Example Application of Surface Roughness

One example application of the surface roughness obtained is to improve the accuracy in determining the core sample's wettability. The wettability is typically studied by contact angle measurements on an ideal surface, but because both the chemical and topological properties of a surface play a role in wettability the roughness should be factored in. Both surface roughness and surface heterogeneity impact the contact angle measurement used to determine wettability. For an ideal smooth surface, the contact angle is equal to an intrinsic contact angle, but a real surface has roughness, and therefore a measured contact angle is measured relative to the line that represents the apparent solid surface. The relationship between surface roughness and wettability is given in Equation (13), where $\theta_m$ is the measured contact angle, $\theta_\gamma$ is the intrinsic Young's contact angle, and r is the surface roughness. When r is equal to 1, the surface is an ideal smooth surface.

$$\cos(\theta_m) = r \cos(\theta_\gamma) \tag{13}$$

In a case where the substrate is flat but heterogeneous and consists of diverse, randomly distributed type of materials, Equation (14) which utilizes a Cassie-Baxter model applies instead of Equation (13). Equation (14) describes an example where the sample material consisting of two different types of materials with the fractions of $f_s$ and $1-f_s$.

$$\cos(\theta_{CB}) = rf_s \cos(\theta_\gamma) + f_s - 1 \tag{14}$$

Using the measured contact angle and surface roughness obtained through the hybrid technique, the intrinsic contact angle of the core sample can be obtained.

In other embodiments of the application, surface roughness may be used to determine other petrophysical parameters such as porosity, relative permeability, electrical properties, nuclear magnetic resonance relaxation times, and saturation profiles in the subsurface formation. Such core analysis may provide important information useful in determining the optimal values for various parameters during formation drilling and hydrocarbon production.

Example Computer Device

Figure 7:
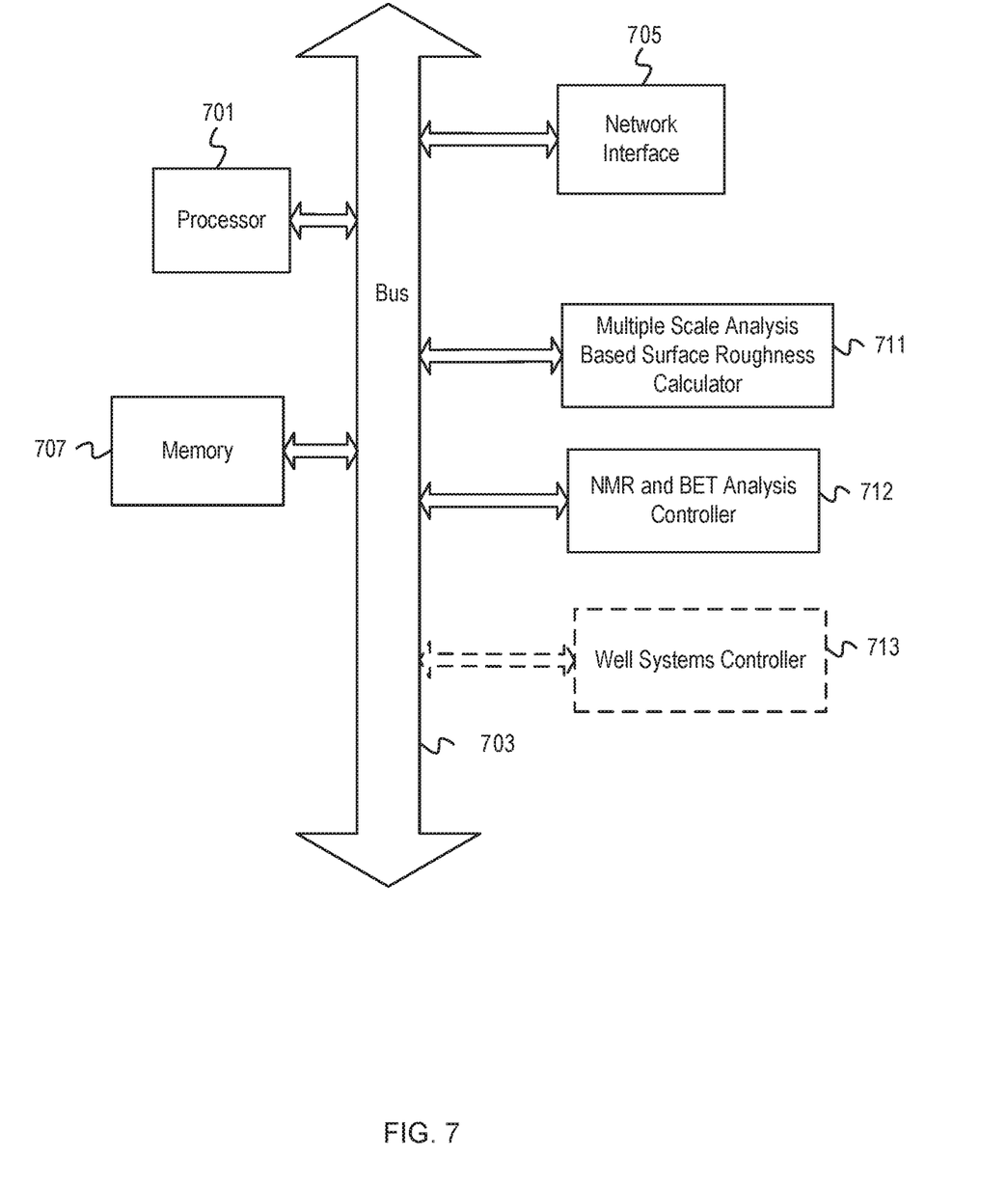
FIG. 7 depicts an example computer capable of executing a hybrid surface roughness determination technique.

FIG. 7 depicts an example computer capable of executing a hybrid surface roughness determination technique. A computer device 700 includes a processor 701 (possibly including multiple processors, multiple cores, multiple nodes, and/or implementing multi-threading, etc.). The computer device 700 includes a memory 707. The memory 707 can be system memory or any one or more of the above already described possible realizations of machine-readable media. The computer device 700 also includes a bus 703 and a network interface 705 (e.g., a Fiber Channel interface, an Ethernet interface, an internet small computer system interface, SONET interface, wireless interface, etc.).

The computer device 700 includes a multiple scale analysis based surface roughness calculator 711 and NMR and BET analysis controller 712. In some cases, the computer device 600 also includes a well system controller 713 depicted in a dashed line as an indication of it being optional. The multiple scale analysis based surface roughness calculator 711 calculate a value representing surface roughness or an estimate of surface roughness. To calculate the surface roughness value, the multiple scale analysis based surface roughness calculator 711 uses the measurements/values from the multiple scale analysis techniques, which in this case are NMR diffusion and gas-adsorption. The NMR and BET analysis controller 712 can perform one or more operations for controlling NMR diffusion and BET equipment. For example, the NMR and BET analysis controller 712 can command equipment to apply an external pulse sequence, for example a CPMG pulse sequence or a diffusion type pulse sequence, to the core sample or to introduce known quantities of nitrogen gas into the sample while recording the relative pressure at a specified temperature(s). The well system controller 713 can also perform one or more operations for controlling a coring system. For example, the well system controller can modify the direction of drillhead, modify the speed of a wireline tool being lowered into a borehole, or bring the drilled core sample to the surface. Any one of the previously described functionalities can be partially (or entirely) implemented in hardware and/or on the processor 701. For example, the functionality can be implemented with an application specific integrated circuit, in logic implemented in the processor 701, in a co-processor on a peripheral device or card, etc. Further, realizations can include fewer or additional components not illustrated in FIG. 7 (e.g., video cards, audio cards, additional network interfaces, peripheral devices, etc.). The processor 701 and the network interface 705 are coupled to the bus 703. Although illustrated as being coupled to the bus 703, the memory 707 can be coupled to the processor 701. The computer device 700 can be integrated into component(s) of the drill pipe downhole and/or be a separate device at the surface that is communicatively coupled to the coring tool for controlling and processing signals (as described herein).

Figure 8:
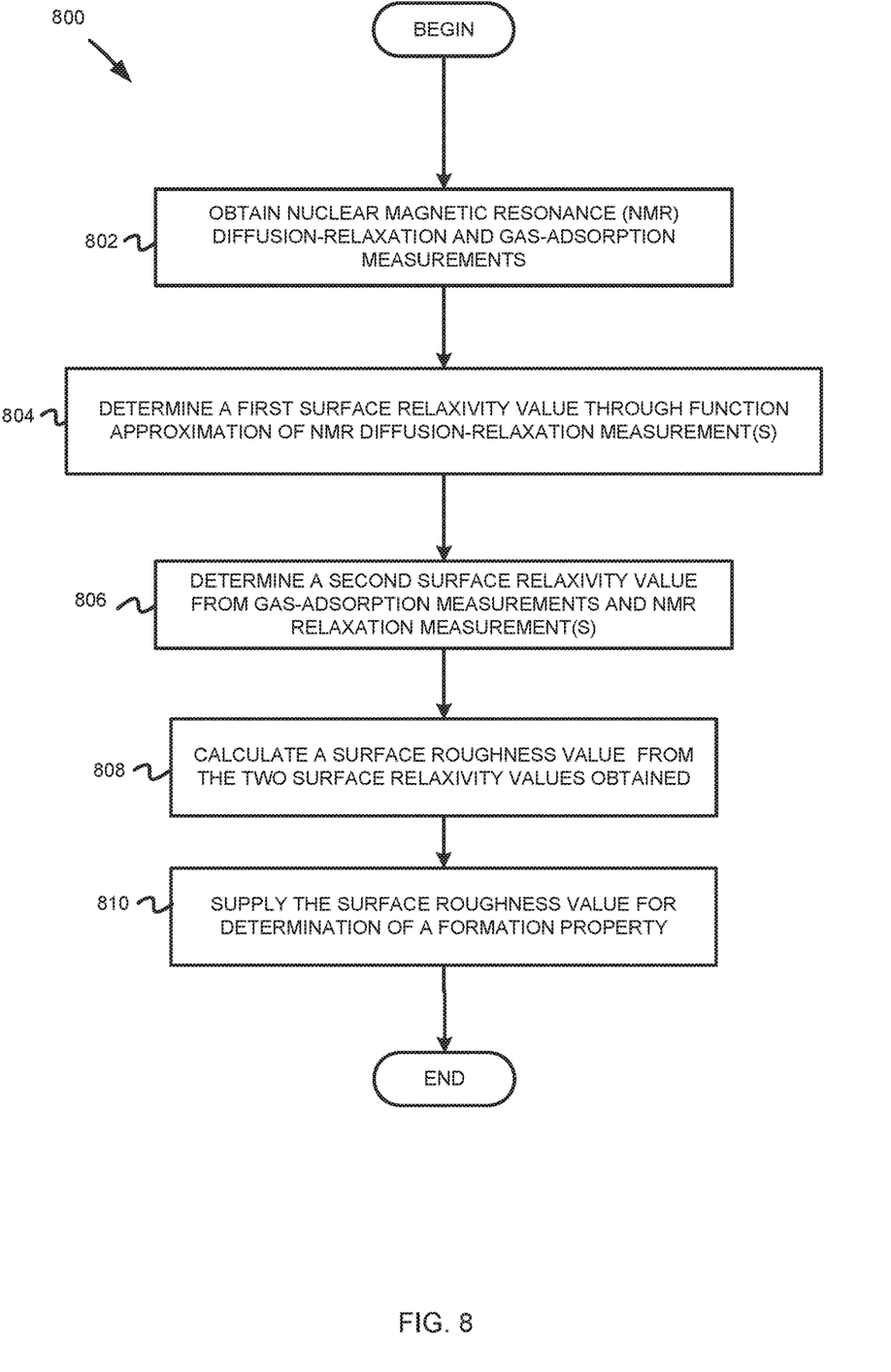
FIG. 8 depicts a flowchart of example operations for determining a surface roughness value from NMR diffusion relaxation and gas adsorption measurements.

As will be appreciated, aspects of the disclosure can be embodied as a system, method or program code/instruction stored in one or more machine-readable media. To illustrate, FIG. 8 is a flowchart 800 of example operations for determining a surface roughness value from NMR diffusion relaxation and gas adsorption measurements. The description of FIG. 8 refers to a "surface roughness estimator" as performing the example operations. The surface roughness estimator is a name that collectively refers to program code/instructions that are executable/interpretable by a computing device to determine a surface roughness value representative of a formation based on measurements of a sample obtained from the formation.

At block 802, the surface roughness estimator obtains NMR diffusion-relaxation and gas-adsorption measurements. For example, the surface roughness estimator may obtain the measurements from a database, file, or transmission. In some cases, the measurements may be communicated directly to the surface roughness estimator from the equipment that took the measurements.

At block 804, the surface roughness estimator determines a first surface relaxivity through function approximation(s) on the NMR diffusion-relaxation measurement(s). The surface roughness estimator can use a Padé approximation of the NMR diffusion-relaxation measurement(s). The function approximation can also be performed with Taylor series. The NMR relaxation measurement can include one or both $T_1$ and $T_2$.

At block 806, the surface roughness estimator determines a second surface relaxivity from gas-adsorption measurements and an NMR relaxation measurement(s). The measurements used to determine the second surface relaxivity can include NMR relaxation distribution measurements and the quantity of adsorbed gas. As indicated in equation 10, part of determining the gas-adsorption based surface relaxivity involves the relationship of the surface area per unit weight of core sample with relaxation time.

At block 808, the surface roughness estimator calculates a surface roughness value from the two surface relaxivity. The surface roughness estimator calculates the surface roughness value as a ratio of the NMR based surface relaxivity value to the gas-adsorption based surface relaxivity value. Calculation of the surface roughness value can further involve modifying the ratio to account for surface modulations.

At block 810, the surface roughness estimator supplies the surface roughness value for determination of one or more petrophysical properties. Examples properties that can be determined with the surface roughness value include wettability, porosity, relative permeability, electrical properties, and saturation profiles in the subsurface formation. The surface roughness estimator can supply the surface roughness value by transmitting the value to another computing device, communicating the value to another program, or storing the value into a repository. In some cases, the program code that implements the surface roughness estimator can also include executable/interpretable instructions to determine one or more of the petrophysical properties of the formation from which a core sample was obtained.

Accordingly, aspects of the system, method or program code/instructions stored in one or more machine-readable media can take the form of hardware, software (including firmware, resident software, micro-code, etc.), or a combination of software and hardware aspects that can all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine-readable medium(s) can be utilized. The machine-readable medium can be a machine-readable signal medium or a machine-readable storage medium. A machine-readable storage medium can be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium can be any tangible medium that can contain or store a program for use by or in connection with an instruction execution system, apparatus, or device. A machine-readable storage medium is not a machine-readable signal medium.

A machine-readable signal medium can include a propagated data signal with machine readable program code embodied therein, for example, in baseband or as part of a carrier wave. Such a propagated signal can take any of a variety of forms, including, but not limited to, electro-magnetic, optical, or any suitable combination thereof. A machine-readable signal medium can be any machine readable medium that is not a machine-readable storage medium and that can communicate, propagate, or transport a program for use by or in connection with an instruction execution system, apparatus, or device.

Program code embodied on a machine-readable medium can be transmitted using any appropriate medium, including but not limited to wireless, wireline, optical fiber cable, RF, etc., or any suitable combination of the foregoing.

Computer program code for carrying out operations for aspects of the disclosure can be written in any combination of one or more programming languages, including an object oriented programming language such as the Java® programming language, C++ or the like; a dynamic programming language such as Python; a scripting language such as Perl programming language or PowerShell script language; and conventional procedural programming languages, such as the "C" programming language or similar programming languages. The program code can execute entirely on a stand-alone machine, can execute in a distributed manner across multiple machines, and can execute on one machine while providing results and or accepting input on another machine.

The program code/instructions can also be stored in a machine-readable medium that can direct a machine to function in a particular manner, such that the instructions stored in the machine-readable medium produce an article of manufacture including instructions which implement the function/act specified in the flowchart and/or block diagram block or blocks.

EXAMPLE EMBODIMENTS

Example embodiments include the following:

Embodiment 1: A method comprising: performing pulsed nuclear magnetic resonance measurements of a core sample to determine a first relaxation measurement; determining a first surface relaxivity of the core sample based, at least in part, on the first relaxation measurement; exposing a subsample of the core sample to a volume of an inert gas and measuring a relative pressure and weight of gas adsorbed on the subsample; determining a second surface relaxivity based, at least in part, on the relative pressure and weight measured; and calculating a surface roughness of a subsurface formation based, at least in part, on the first and second surface relaxivities, wherein the core sample was obtained from the subsurface formation.

Embodiment 2: The method of Embodiment 1, wherein calculating the surface roughness comprises calculating a surface roughness value as a ratio of the first surface relaxivity and the second surface relaxivity.

Embodiment 3: The method of Embodiment 2, wherein the ratio between the first and second surface relaxivities is determined by dividing the first surface relaxivity over the second surface relaxivity and factoring in a percentage of the surface that is covered by a surface modulation.

Embodiment 4: The method of any one of Embodiments 1-3, wherein calculating the surface roughness further comprises accounting for surface modulation that models the roughness of the core sample.

Embodiment 5: The method of Embodiment 4, wherein accounting for the surface modulation that models the surface roughness of the core sample comprises approximating through cylindrical shapes.

Embodiment 6: The method of any one of Embodiments 1-5, further comprising determining an intrinsic contact angle of the core sample based, at least in part, on the calculated surface roughness.

Embodiment 7: The method of Embodiment 6, wherein determining the intrinsic contact angle of the core sample utilizes the Cassie-Baxter model.

Embodiment 8: The method of any one of Embodiments 1-7, wherein the core sample is a drilling cutting.

Embodiment 9: The method of any one of Embodiments 1-8, wherein determining the first surface relaxivity is also based on a 2D diffusion-relaxation correlation map and determining the second relaxivity is further based on a 1D relaxation distribution.

Embodiment 10: The method of any one of Embodiments 1-9, wherein exposing the core sample to volume of gas and subsequent measurements comprises performing a Brunauer-Emmett-Teller gas-adsorption technique on the core sample.

Embodiment 11: The method of any one of Embodiments 1-10 further comprising cleaning and drying the core sample before performing the pulsed nuclear magnetic resonance measurements and before exposing the core sample to the volume of gas.

Embodiment 12: A method comprising: obtaining a diffusion-relaxation time for a core sample from a subsurface formation; determining a first surface relaxivity of the core sample based, at least in part, on the diffusion-relaxation time; determining a second surface relaxivity of the core sample based, at least in part, on a relaxation measurement and relative pressure and weight obtained from gas-adsorption analysis of the core sample; and estimating surface roughness of the subsurface formation based, at least in part, on the first and second surface relaxivities.

Embodiment 13: The method of Embodiment 12 further comprising: performing pulsed nuclear magnetic resonance diffusion-relaxation analysis on the core sample to obtain the diffusion-relaxation time; and performing the gas-adsorption analysis on the core sample.

Embodiment 14: The method of Embodiments 12 or 13 further comprising cleaning and drying the core sample before the nuclear magnetic resonance diffusion-relaxation analysis and the gas-adsorption analysis.

Embodiment 15: The method of any one of Embodiments 12-14, wherein estimating surface roughness comprises calculating a surface roughness value as a ratio of the first surface relaxivity and the second surface relaxivity.

Embodiment 16: The method of Embodiment 15, wherein calculating the ratio between the first and second surface relaxivities comprises dividing the first surface relaxivity over the second surface relaxivity and factoring in a percentage of a surface of the core sample that is covered by a surface modulation.

Embodiment 17: The method of any one of Embodiments 12-16 further comprising determining with the surface roughness estimate at least one of wettability, porosity, permeability, relative permeability, pore size, and capillarity.

Embodiment 18: A non-transitory machine-readable medium having stored thereon program code executable by a computing device, the program code comprising instructions to: determine a first surface relaxivity at a first average length-scale for a core sample; determine a second surface relaxivity at a second average length-scale for the core sample, wherein the first average length-scale and the second average length-scale differ by multiple orders of magnitude; and indicate a surface roughness value based, at least in part, on a ratio of the first surface relaxivity and the second surface relaxivity.

Embodiment 19: The non-transitory machine-readable medium of Embodiment 18, wherein the program code further comprises instructions to indicate the surface roughness value also based, at least in part, on a percentage of a surface of the core sample covered by surface modulation.

Embodiment 20: The non-transitory machine-readable medium of Embodiments 18 or 19, wherein the program code further comprises instructions that control equipment to: perform pulsed nuclear magnetic resonance diffusion-relaxation measurements on the core sample to determine the first surface relaxivity; and perform gas-adsorption analysis on the core sample to obtain the second surface relaxivity.

What is claimed is:

1. A method comprising:
performing pulsed nuclear magnetic resonance measurements of a core sample to determine a first relaxation measurement;
determining a first surface relaxivity of the core sample based, at least in part, on the first relaxation measurement;
exposing a subsample of the core sample to a volume of an inert gas and measuring a relative pressure and weight of gas adsorbed on the subsample;
determining a second surface relaxivity based, at least in part, on the relative pressure and weight measured; and
calculating a surface roughness of a subsurface formation based, at least in part, on the first and second surface relaxivities, wherein the core sample was obtained from the subsurface formation.

2. The method of claim 1, wherein calculating the surface roughness comprises calculating a surface roughness value as a ratio of the first surface relaxivity and the second surface relaxivity.

3. The method of claim 2, wherein the ratio between the first and second surface relaxivities is determined by dividing the first surface relaxivity over the second surface relaxivity and factoring in a percentage of the surface that is covered by a surface modulation.

4. The method of claim 1, wherein calculating the surface roughness further comprises accounting for surface modulation that models the roughness of the core sample.

5. The method of claim 4, wherein accounting for the surface modulation that models the surface roughness of the core sample comprises approximating through cylindrical shapes.

6. The method of claim 1, further comprising determining an intrinsic contact angle of the core sample based, at least in part, on the calculated surface roughness.

7. The method of claim 6, wherein determining the intrinsic contact angle of the core sample utilizes the Cassie-Baxter model.

8. The method of claim 1, wherein the core sample is a drilling cutting.

9. The method of claim 1, wherein determining the first surface relaxivity is also based on a 2D diffusion-relaxation correlation map and determining the second relaxivity is further based on a 1D relaxation distribution.

10. The method of claim 1, wherein exposing the core sample to volume of gas and subsequent measurements comprises performing a Brunauer-Emmett-Teller gas-adsorption technique on the core sample.

11. The method of claim 1 further comprising cleaning and drying the core sample before performing the pulsed nuclear magnetic resonance measurements and before exposing the core sample to the volume of gas.

12. A method comprising:
obtaining a diffusion-relaxation time for a core sample from a subsurface formation:
determining a first surface relaxivity of the core sample based, at least in part, on the diffusion-relaxation time;
determining a second surface relaxivity of the core sample based, at least in part, on a relaxation measurement and relative pressure and weight obtained from gas-adsorption analysis of the core sample; and
estimating surface roughness of the subsurface formation based, at least in part, on the first and second surface relaxivities.

13. The method of claim 12 further comprising:
performing pulsed nuclear magnetic resonance diffusion-relaxation analysis on the core sample to obtain the diffusion-relaxation time; and
performing the gas-adsorption analysis on the core sample.

14. The method of claim 13 further comprising cleaning and drying the core sample before the nuclear magnetic resonance diffusion-relaxation analysis and the gas-adsorption analysis.

15. The method of claim 12, wherein estimating surface roughness comprises calculating a surface roughness value as a ratio of the first surface relaxivity and the second surface relaxivity.

16. The method of claim 15, wherein calculating the ratio between the first and second surface relaxivities comprises dividing the first surface relaxivity over the second surface relaxivity and factoring in a percentage of a surface of the core sample that is covered by a surface modulation.

17. The method of claim 12 further comprising determining with the surface roughness estimate at least one of wettability, porosity, permeability, relative permeability, pore size, and capillarity.

18. A non-transitory machine-readable medium having stored thereon program code executable by a computing device, the program code comprising instructions to:
   determine a first surface relaxivity at a first average length-scale for a core sample;
   determine a second surface relaxivity at a second average length-scale for the core sample, wherein the first average length-scale and the second average length-scale differ by multiple orders of magnitude; and
   indicate a surface roughness value based, at least in part, on a ratio of the first surface relaxivity and the second surface relaxivity.

19. The non-transitory machine-readable medium of claim 18, wherein the program code further comprises instructions to indicate the surface roughness value also based, at least in part, on a percentage of a surface of the core sample covered by surface modulation.

20. The non-transitory machine-readable medium of claim 18, wherein the program code further comprises instructions that control equipment to:
   perform pulsed nuclear magnetic resonance diffusion-relaxation measurements on the core sample to determine the first surface relaxivity; and
   perform gas-adsorption analysis on the core sample to obtain the second surface relaxivity.

* * * * *